(12) United States Patent
Huang et al.

(10) Patent No.: US 8,858,512 B2
(45) Date of Patent: Oct. 14, 2014

(54) INJECTOR

(75) Inventors: Yi-Hsin Huang, New Taipei (TW);
Chih-Chiang Yang, New Taipei (TW);
Chao-Wang Chen, New Taipei (TW)

(73) Assignee: Taidoc Technology Corporation, New Taipei (TW)

( * ) Notice: Subject to any disclaimer, the term of this patent is extended or adjusted under 35 U.S.C. 154(b) by 183 days.

(21) Appl. No.: 13/429,442

(22) Filed: Mar. 26, 2012

(65) Prior Publication Data
US 2012/0253293 A1 Oct. 4, 2012

(30) Foreign Application Priority Data
Apr. 1, 2011 (TW) .............................. 100111710 A

(51) Int. Cl.
*A61M 5/00* (2006.01)
*A61M 5/315* (2006.01)
*A61M 5/24* (2006.01)

(52) U.S. Cl.
CPC ....... *A61M 5/31551* (2013.01); *A61M 5/31556* (2013.01); *A61M 2205/581* (2013.01); *A61M 5/31585* (2013.01); *A61M 2005/2407* (2013.01)
USPC ............ 604/209; 604/207; 604/211; 604/224

(58) Field of Classification Search
CPC .......... A61M 5/31551; A61M 5/3155; A61M 5/31548; A61M 5/31533; A61M 5/31558; A61M 5/31585; A61M 5/31586; A61M 5/31583; A61M 5/31576; A61M 5/31565; A61M 5/178; A61M 5/00
USPC ......................... 604/207–211, 224, 228, 229
See application file for complete search history.

(56) References Cited

U.S. PATENT DOCUMENTS 4,865,591 A * 9/1989 Sams ............................ 604/186
5,679,111 A * 10/1997 Hjertman et al. ............. 604/135

* cited by examiner

*Primary Examiner* — Bhisma Mehta
*Assistant Examiner* — Bradley G Thomas, Jr.
(74) *Attorney, Agent, or Firm* — Chun-Ming Shih

(57) ABSTRACT

The present invention related to an injector is provided. The injector includes a case body, a dose setting, a first engagement, a second engagement, an elasticity element, and a button. The dose setting is used to preset a dose. The first engagement is connected with the dose setting. The elasticity element is connected between the first engagement and the second engagement. When the elasticity element is in an extension state, the first engagement and the second engagement are separated. When the button is pushed, the elasticity element is entered into a compress state to combine the first engagement and the second engagement, and then push the dose setting.

6 Claims, 16 Drawing Sheets

INJECTOR

BACKGROUND OF THE INVENTION

1. Field of the Invention

The present invention relates in general to an injector, and particularly relates to an injector for freely presetting a dose.

2. Description of the Related Art

In the past, insulin injection is drawing drugs with the syringe then to carry out the injection. The procedure of drawing drugs is complication and hard to control the drawing dosage. Moreover, it is quit inconvenient for users to use many implements. Therefore, an insulin injector is designed for users to get more conveniently with insulin injection.

A conventional insulin injector needs to preset a dose before injection. To be noticed, when preset over a desired dose, it has to zeroing then reset the dose, and that is not convenient for users.

Further, there is usually a button in a posterior of the conventional insulin injector. When users pushed the button by mistake, the drug will leak from a needle of the insulin injector to cause an inaccuracy of injecting dose and even induce serious harm indirectly for users. Thus, a need exists for improved the device such as injector.

SUMMARY OF THE INVENTION

According to one aspect of the present invention is to provide an injector for preventing from pushing a button by mistake to cause leaky of liquid agent within the injector.

In one aspect, the present invention provides an injector for freely presetting a dose.

In a preferred embodiment of the present invention, the present invention provides an injector, including a case body, a dose setting, a drive stem, a first linkage, a first engagement, a second engagement, a first elasticity element and a button. The case body has a first thread. The dose setting has a second thread assembled to the first thread, and a first fastener. The dose setting can move relatively with the case body through the first thread and the second thread so as to preset a dose. The drive stem has a third thread for pushing a dosage can. The first linkage has a second fastener, a first rotatable fastener and a third fastener. The second fastener is used to clasp with the first fastener. The first engagement has a fourth fastener and a first toothed clutch. The fourth fastener is used to clasp with the third fastener. The second engagement has a second toothed clutch and a first groove. The second toothed clutch is engaged with the first toothed clutch. The second linkage has a second groove and a fourth thread. The second groove is assembled to the first groove. The fourth thread is assembled to the third thread. The first elasticity element is connected between the first engagement and the second engagement. When the elasticity element is in an extension state, the first engagement and the second engagement are separated. The button has a second rotatable fastener for clasping with the first rotatable fastener. When the button is pushed, the elasticity element is entered into a compress state to combine the first engagement and the second engagement, and then push the dose setting.

In an embodiment in accordance with the present invention, the injector further includes a third engagement, a second elasticity element and a fourth engagement. The third engagement has a first ratchet, a third toothed clutch, a fifth fastener and a first bond element. The fourth engagement has a fourth toothed clutch, a sixth fastener and a chute opening. The fourth toothed clutch is used to clasp with the third toothed clutch. The sixth fastener is used to clasp with the fifth fastener so that the second elasticity element is connected between the third engagement and the fourth engagement. The second linkage further has a second ratchet. The second ratchet is assembled to the first ratchet. The case body further has a second bond element. The second bond element is used to clasp with the first bond element. The drive stem further has a chute for axially sliding in the chute opening.

In an embodiment in accordance with the present invention, the injector further includes a stem cap. The stem cap is connected with an anterior end of drive stem. In another embodiment, the injector further includes a can casing. The can casing has a third bond element. The case body further has a fourth bond element for clasping with the third bond element. When the dosage can is disposed on an anterior end of stem cap, the second elasticity element is in a compress state to combine the fourth toothed clutch and the third toothed clutch. When the dosage can is removed from the anterior end of stem cap, the second elasticity element is in an extension state to uninstall the fourth toothed clutch and the third toothed clutch.

In an embodiment in accordance with the present invention, the case body further has a dosage window. The dose setting further has a plurality dosage marks. One of the dosage marks description above is shown in the dosage window for displaying the injected dosage.

In an embodiment in accordance with the present invention, the injector further includes a third linkage. The third linkage has a first track and a third ratchet. The dose setting further has a second track assembled with the first track. The case body further has a fourth ratchet connected with the third ratchet. When the dose setting is rotated, the second track and the first track bring the third linkage to rotate and the fourth ratchet is interfered with the third ratchet.

In another aspect in accordance with the present invention, the present invention provides an injector, including a case body, a dose setting, a drive stem, a first engagement, a second engagement, a first elasticity element and a button. The dose setting is moved relatively with the case body so as to preset a dose. The drive stem is used to push the dosage can. The first engagement is moved relatively with the dose setting. The second engagement is moved relatively with the drive stem. The first elasticity element is connected between the first engagement and the second engagement. When the first elasticity element is in an extension state, the first engagement and the second engagement are separated. The button is coupled with the first engagement. When the button is pushed, the first elasticity element is entered into a compress state to combine the first engagement and the second engagement, and then push the dose setting.

According to the aspect of the present invention as description above, the injector is disposed the first engagement and the second engagement between the button and the drive stem. The button is pushed to combine the first engagement and the second engagement so as to connect with the drive stem. As a result, it prevents the problem of drugs leaky and inaccuracy of injected dosage caused by pushed the button mistakenly.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF THE PREFERRED EMBODIMENTS

Figure 1A:
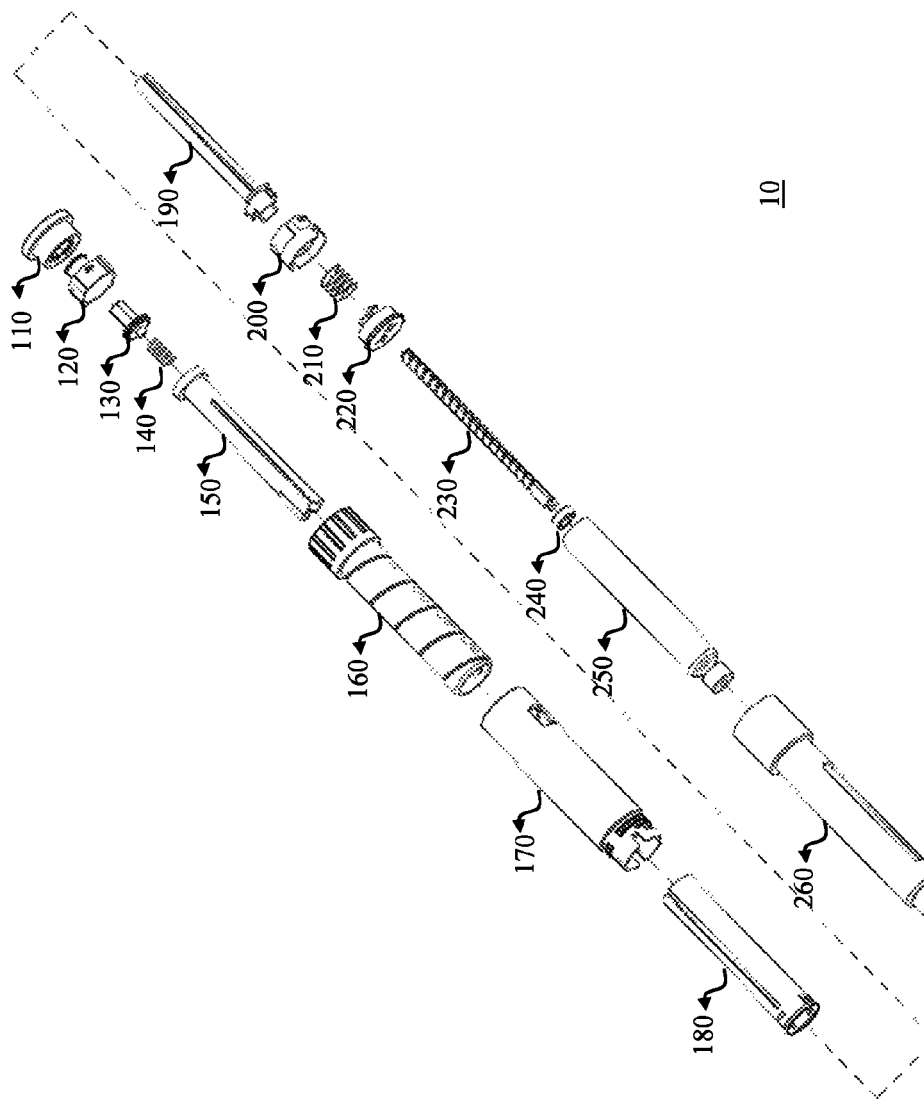
FIG. 1A is an exploded schematic perspective view of an embodiment of an injector in accordance with the present invention.

For the purposes of promoting an understanding of the principles of the invention, reference will now be made to the embodiment illustrated in the drawings, and specific language will be used to describe that embodiment. It will nevertheless be understood that no limitation of the scope of the invention is intended. Alterations and modifications in the illustrated device, and further applications of the principles of the invention as illustrated therein, as would normally occur to one skilled in the art to which the invention relates are contemplated, are desired to be protected. Such alternative embodiments require certain adaptations to the embodiments discussed herein that would be obvious to those skilled in the art.

The following description and accompanying drawings are some examples in accordance with the present invention. The same symbol herein in the drawings indicates the same or similar structure.

Figure 1B:
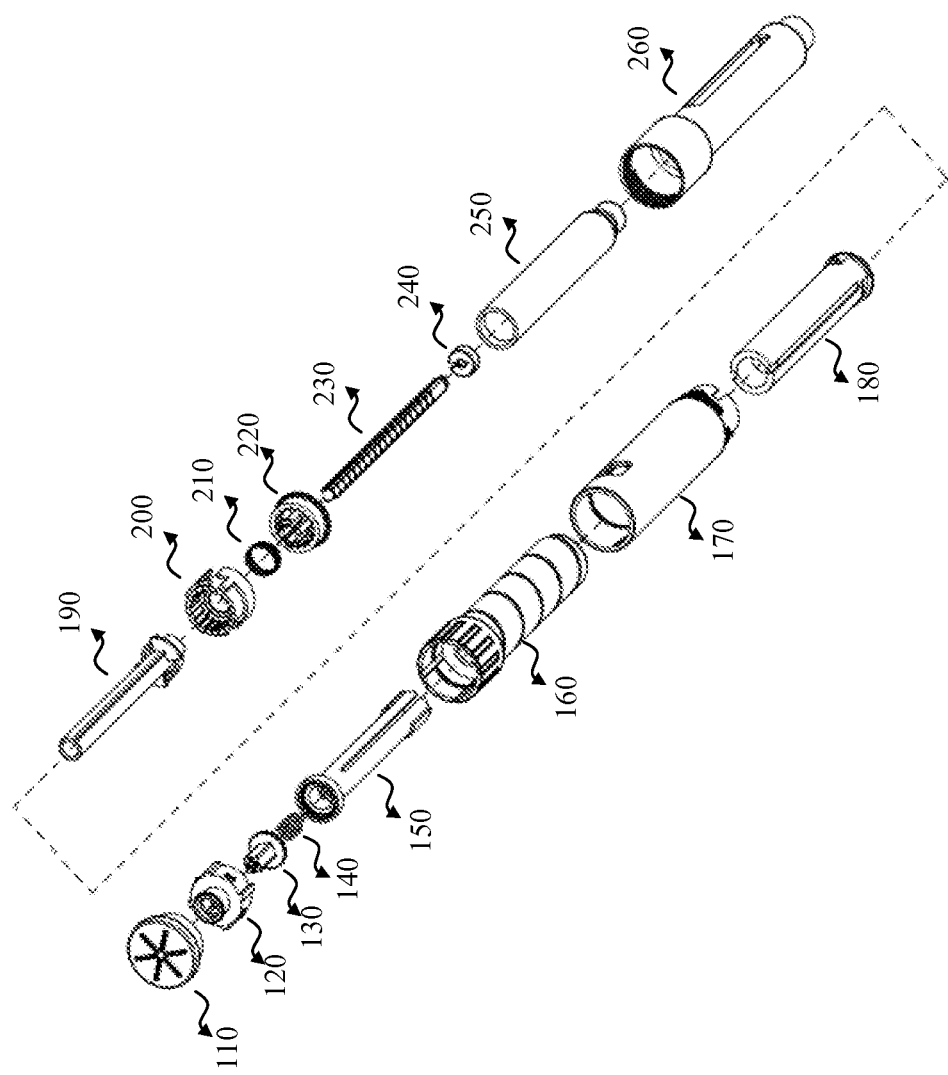
FIG. 1B is an exploded schematic perspective view of another side of the injector in FIG. 1A.
Figure 2A:
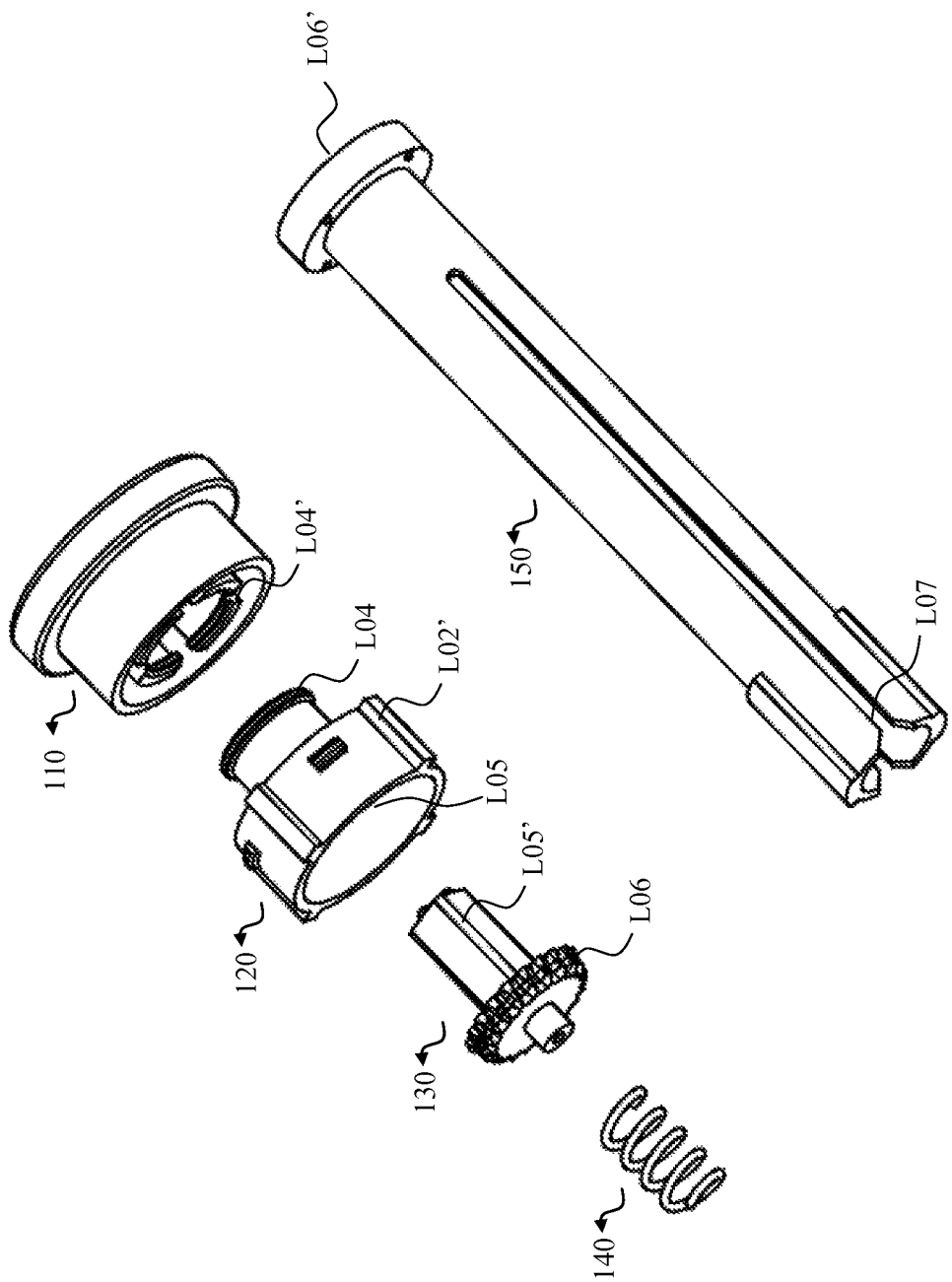
FIG. 2A is a first partial enlarge schematic perspective view of the injector in FIG. 1A.
Figure 2B:
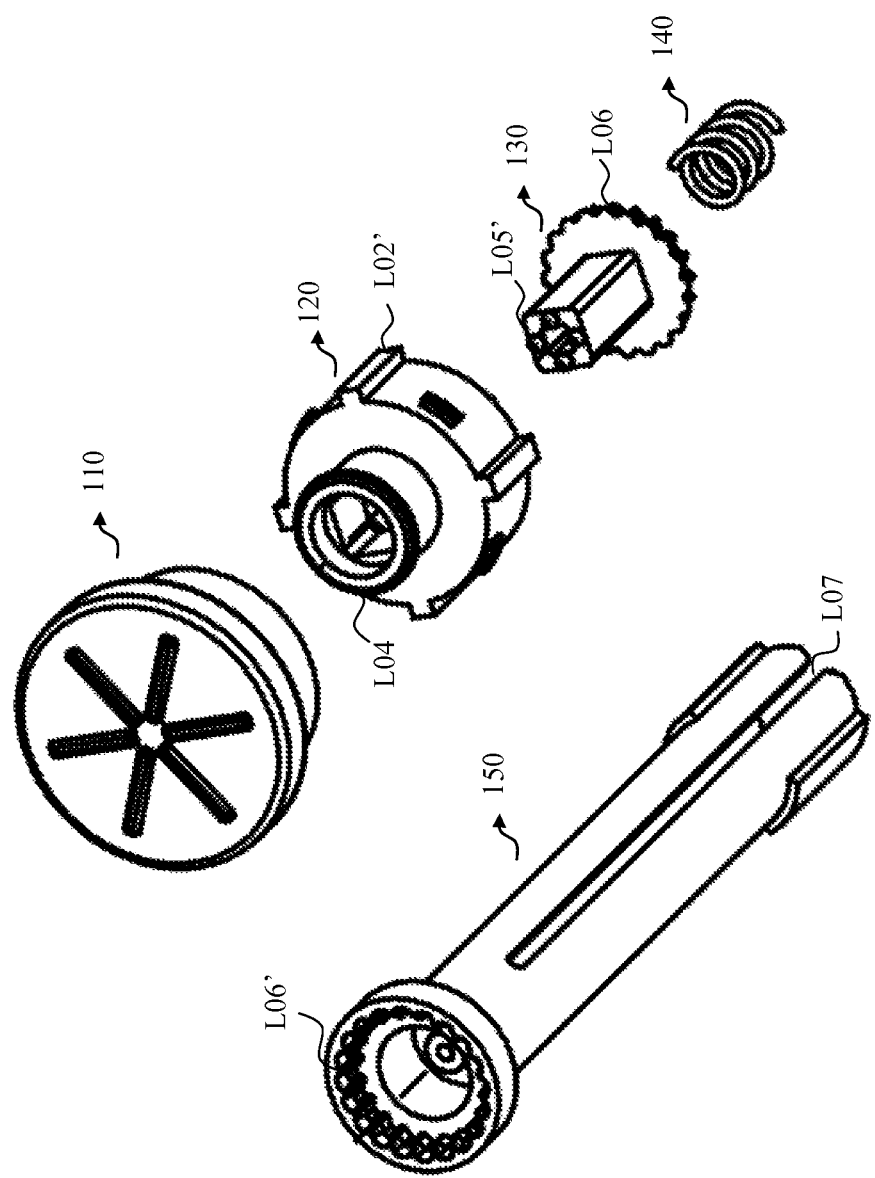
FIG. 2B is a partial enlarge schematic perspective view of another side of the injector in FIG. 2A.
Figure 3A:
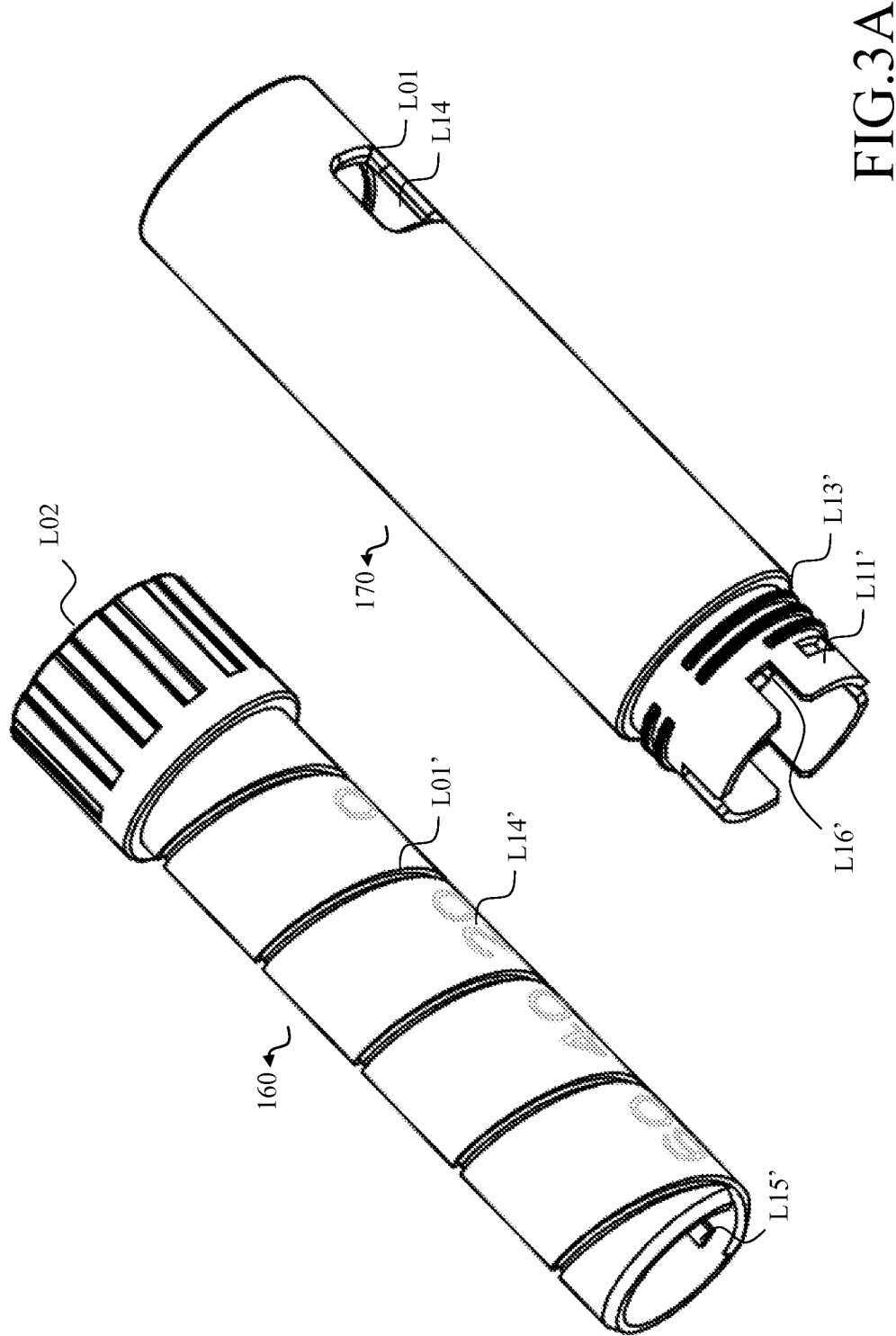
FIG. 3A is a second partial enlarge schematic perspective view of the injector in FIG. 1A.
Figure 3B:
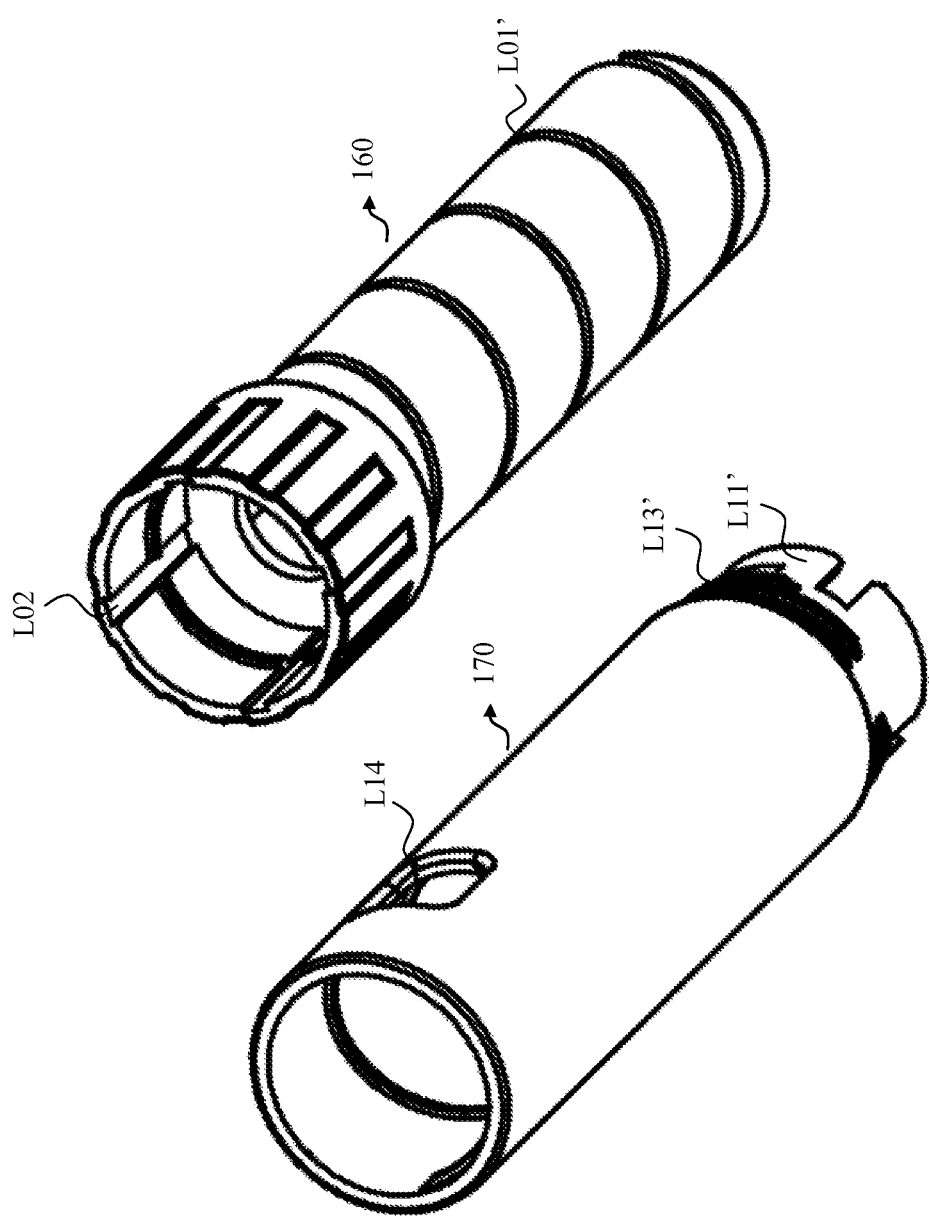
FIG. 3B is a partial enlarge schematic perspective view of another side of the injector in FIG. 3A.
Figure 4A:
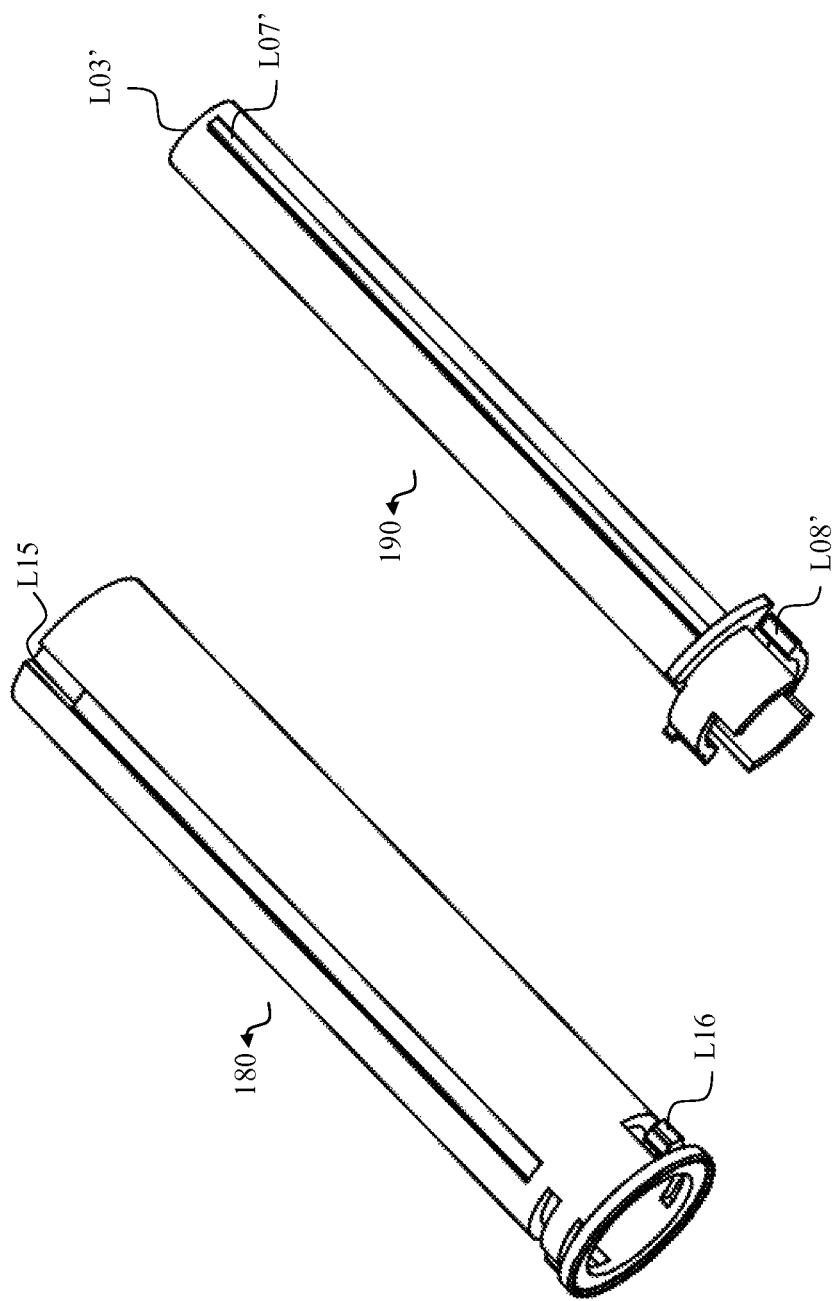
FIG. 4A is a third partial enlarge schematic perspective view of the injector in FIG. 1A.
Figure 4B:
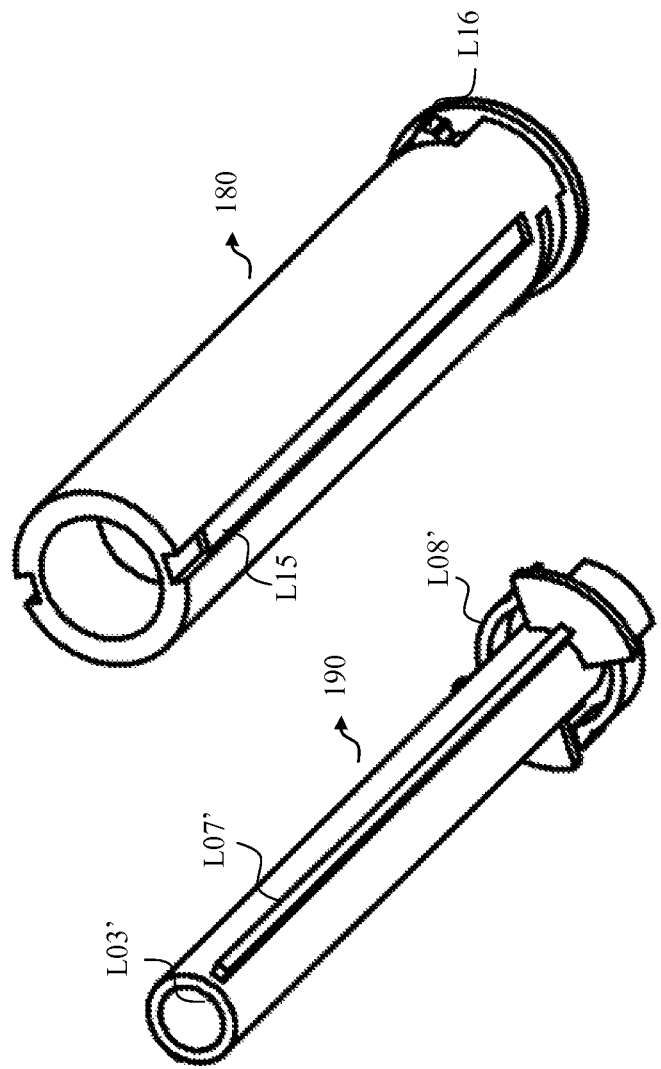
FIG. 4B is a partial enlarge schematic perspective view of another side of the injector in FIG. 4A.
Figure 5A:
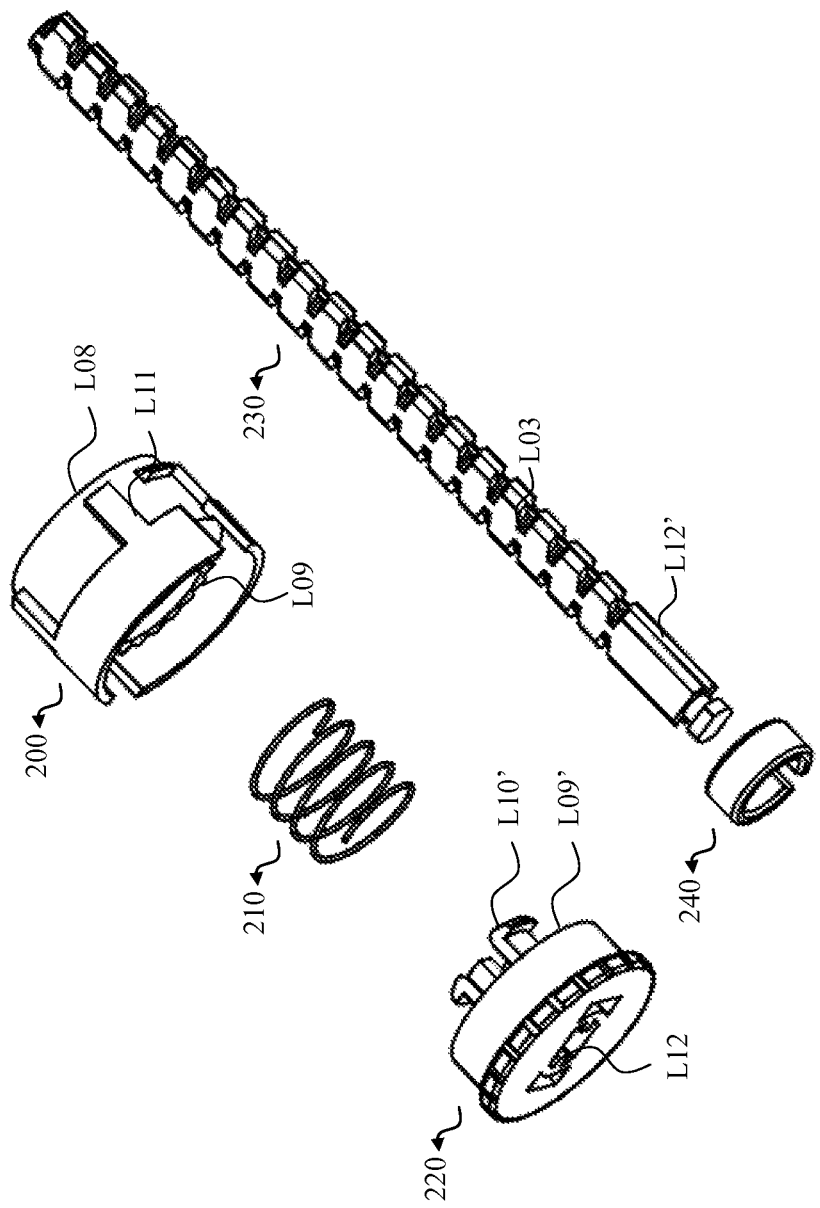
FIG. 5A is a fourth partial enlarge schematic perspective view of the injector in FIG. 1A.
Figure 5B:
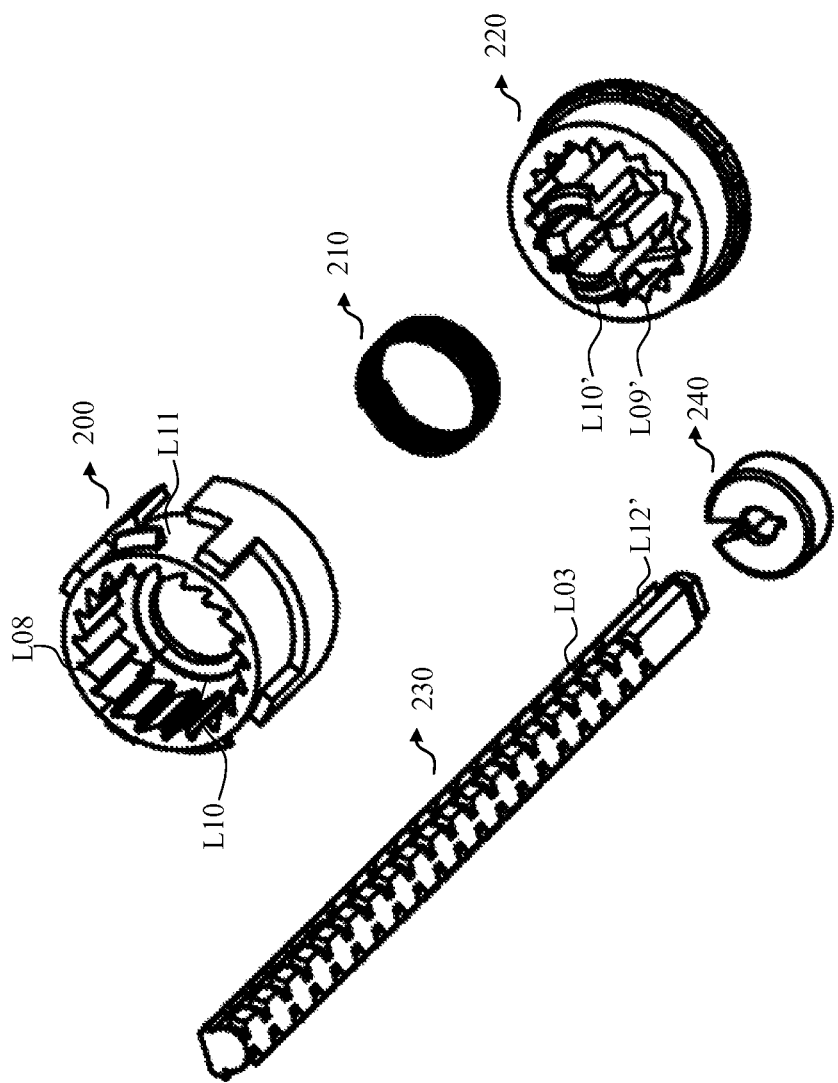
FIG. 5B is a partial enlarge schematic perspective view of another side of the injector in FIG. 5A.
Figure 6A:
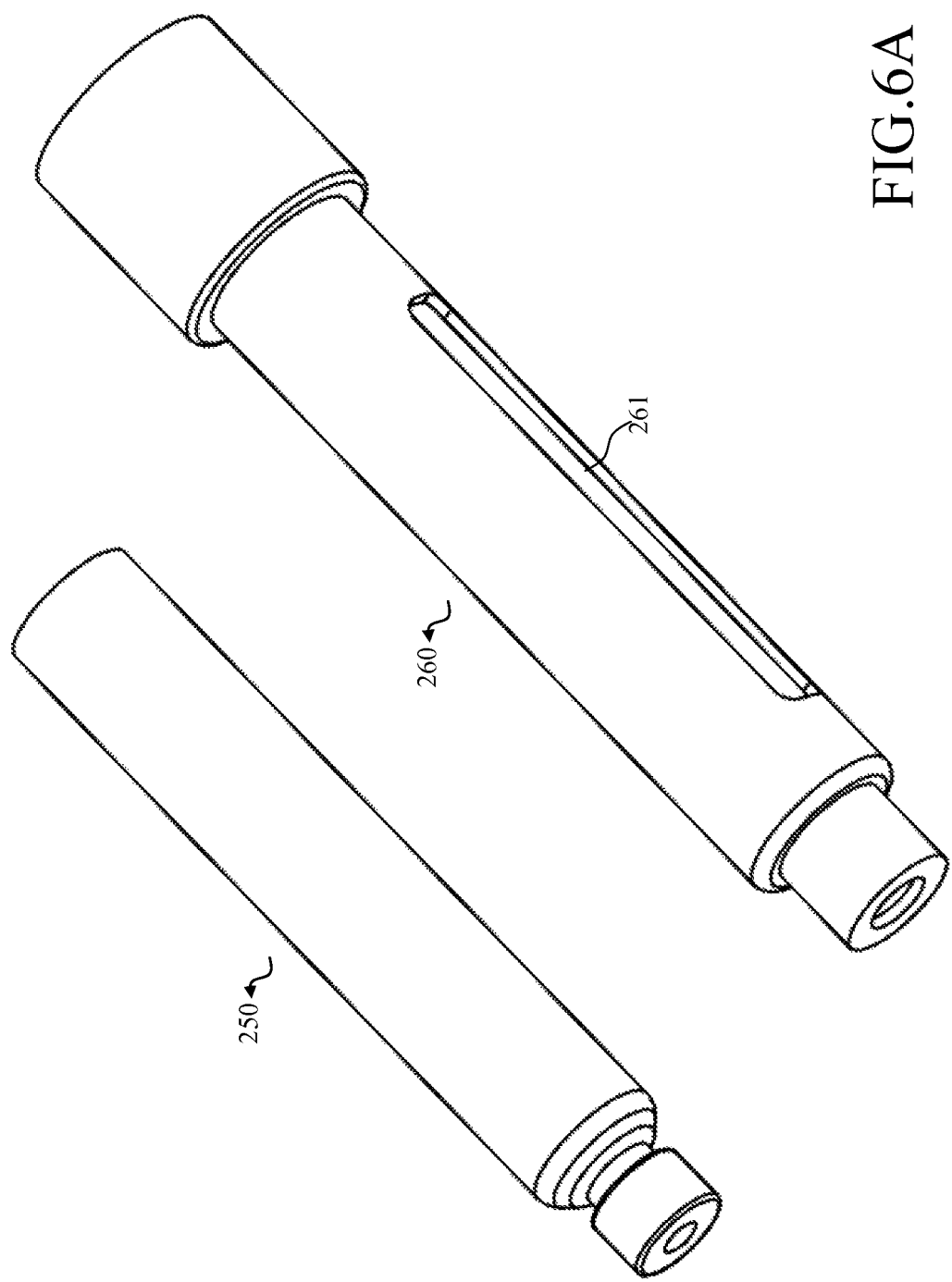
FIG. 6A is a fifth partial enlarge schematic perspective view of the injector in FIG. 1A.
Figure 6B:
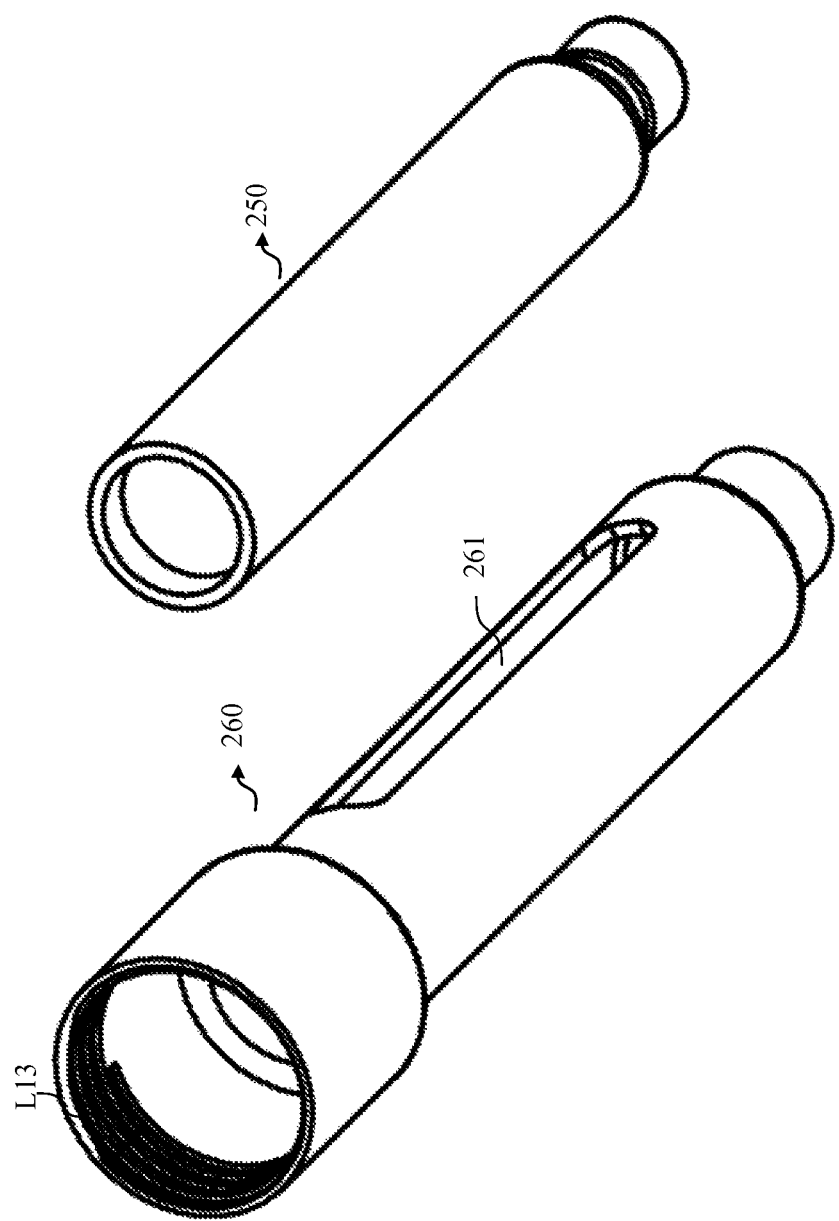
FIG. 6B is a partial enlarge schematic perspective view of another side of the injector in FIG. 6A.

With reference to FIG. 1, it is an exploded schematic perspective view of an embodiment of an injector in accordance with the present invention. FIG. 1B is an exploded schematic perspective view of another side of the injector in FIG. 1A. FIG. 2A is a first partial enlarge schematic perspective view of the injector in FIG. 1A. FIG. 2B is a partial enlarge schematic perspective view of another side of the injector in FIG. 2A. FIG. 3A is a second partial enlarge schematic perspective view of the injector in FIG. 1A. FIG. 3B is a partial enlarge schematic perspective view of another side of the injector in FIG. 3A. FIG. 4A is a third partial enlarge schematic perspective view of the injector in FIG. 1A. FIG. 4B is a partial enlarge schematic perspective view of another side of the injector in FIG. 4A. FIG. 5A is a fourth partial enlarge schematic perspective view of the injector in FIG. 1A. FIG. 5B is a partial enlarge schematic perspective view of another side of the injector in FIG. 5A. FIG. 6A is a fifth partial enlarge schematic perspective view of the injector in FIG. 1A. FIG. 6B is a partial enlarge schematic perspective view of another side of the injector in FIG. 6A. Please refer to FIGS. 1A to 6B in combination. In the present embodiment, an injector 10 has an illustration of insulin injector for instance, but the present invention shall not be limited for this. In other embodiment, the injector 10 is perhaps used to inject other solutions or drugs.

In the present embodiment, the injector 10 comprises a button 110, a first linkage 120, a first engagement 130, a first elasticity element 140, a second engagement 150, a dose setting 160, a case body 170, a third linkage 180, a second linkage 190, a third engagement 200, a second elasticity element 210, a fourth engagement 220, a drive stem 230, a stem cap 240 and a can casing 260, but the present invention shall not be limited for this. Those skilled in the art can change the construction of injector 10 to other type by their demand, for example, it could be added, deleted or replaced the structure of injector 10. The following are more detailed description of each element. Table 1 is a subordinate relationship of each structure. Please refer to Table 1 in combination.

TABLE 1

The subordinate relationship of each structure
(This is a simple form only presented by mark)
subordinate relationship

| |
| --- |
| L04'∈110 |
| L02', L04, L05∈120 |
| L05', L06∈130 |
| L06', L07∈150 |
| L01', L02, L14', L15'∈160 |
| L01, L11', L13', L14, L16'∈170 |
| L15, L16∈180 |
| L03', L07', L08'∈190 |
| L08, L09, L10, L11∈200 |
| L09', L10', L12∈220 |
| L03, L12'∈230 |
| L13∈260 |

The button 110 includes a second rotatable fastener L04'. The first linkage 120 includes a second fastener L02', a first rotatable fastener L04 and a third fastener L05. The first engagement 130 includes a fourth fastener L05' and a first toothed clutch L06. A second engagement 150 includes a second toothed clutch L06' and a first groove L07. A dose setting 160 includes a second thread L01', a first fastener L02, a plurality of dosage marks L14' and a second track L15'. A case body 170 includes a first thread L01, a second bond element L11', a fourth bond element L13', a dosage window L14 and a fourth ratchet L16'.

Following the description above, the third linkage 180 includes a first track L15 and a third ratchet L16. A second linkage 190 includes a fourth thread L03', a second groove L07' and a second ratchet L08'. A third engagement 200 includes a first ratchet L08, a third toothed clutch L09, a fifth fastener L10 and a first bond element L11. A fourth engagement 220 includes a fourth toothed clutch L09', a sixth fastener L10' and a chute opening L12. A drive stem 230 includes a third thread L03 and a chute L12'. A can casing 260 includes a third bond element L13.

TABLE 2

The interdependence and subordinate relationship of each structure
(This is a simple form only presented by mark)

| Interdependence | Subordinate | Subordinate |
| --- | --- | --- |
| L01 to L01' | L01∈170 | L01'∈160 |
| L02 to L02' | L02∈160 | L02'∈120 |

TABLE 2-continued

The interdependence and subordinate relationship of each structure
(This is a simple form only presented by mark)

| Interdependence | Subordinate | Subordinate |
|---|---|---|
| L03 to L03' | L03∈230 | L03'∈190 |
| L04 to L04' | L04∈120 | L04'∈110 |
| L05 to L05' | L05∈120 | L05'∈130 |
| L06 to L06' | L06∈130 | L06'∈150 |
| L07 to L07' | L07∈150 | L07'∈190 |
| L08 to L08' | L08∈200 | L08'∈190 |
| L09 to L09' | L09∈200 | L09'∈220 |
| L10 to L10' | L10∈200 | L10'∈220 |
| L11 to L11' | L11∈200 | L11'∈170 |
| L12 to L12' | L12∈220 | L12'∈230 |
| L13 to L13' | L13∈260 | L13'∈170 |
| L14 to L14' | L14∈170 | L14'∈160 |
| L15 to L15' | L15∈180 | L15'∈160 |
| L16 to L16' | L16∈180 | L16'∈170 |

Please refer to Table 2 in combination. The first thread L01 of the case body 170 is assembled with the second thread L01' of the dose setting 160. The dose setting 160 is connected with the case body 170 through the first thread L01 and the second thread L01' to preset a dose. More specifically, the dose setting 160 and the case body 170 are rotated with each other so as to cause an axially moving.

The first fastener L02 of the dose setting 160 is used to clasp with a second fastener L02' of the first linkage 120. The dose setting 160 is connected with the first linkage 120 to rotate together through the first fastener L02 and the second fastener L02'.

The third thread L03 of the drive stem 230 is assembled with the fourth thread L03' of the second linkage 190. The drive stem 230 is moved relatively to the second linkage 190 through the third thread L03 and the fourth thread L03'. More specifically, the drive stem 230 and the second linkage 190 are rotated relatively to each other so as to cause an axially moving.

The first rotatable fastener L04 of the first linkage 120 is used to clasp with the second rotatable fastener L04' of the button 110. After clasped, rotating the button 110 will not rotate the first linkage 120 relatively.

The third fastener L05 of the first linkage 120 is used to clasp with the fourth fastener L05' of the first engagement 130. In the present embodiment, the third fastener L05 is a square concave and the fourth fastener L05' is a corresponding square protruding, but the present invention shall not be limited for this. In other embodiment, it could be other type of the fastener such as triangle, pentagon and so on. After clasped, the first linkage 120 is connected with the first engagement 130 to rotate together.

The first toothed clutch L06 of the first engagement 130 is engaged with the second toothed clutch L06' of the second engagement 150. To be noticed, the first elasticity element 140 is assembled between the first engagement 130 and the second engagement 150. When the first elasticity element 140 is in an extension state, the first engagement 130 and the second engagement 150 are separated and can not connect with each other. When the first elasticity element 140 is in a compress state, the first toothed clutch L06 is engaged with the second toothed clutch L06' so that the first engagement 130 is connected with the second engagement 150 to rotate relatively.

The first groove L07 of the second engagement 150 is assembled to the second groove L07' of the second linkage 190. The second engagement 150 is axially sliding with the second linkage 190 and they are rotating together through the first groove L07 and the second groove L07'.

The first ratchet L08 of the third engagement 200 is assembled with the second ratchet L08' of the second linkage 190. By interference between the first ratchet L08 and the second ratchet L08', the second linkage 190 and the third engagement 200 are only rotated in solo-direction and not rotated in bi-direction. The way of advantage is making sure that the drive stem 230 only move forwardly but not back off.

The third toothed clutch L09 of the third engagement 200 is engaged with the fourth toothed clutch L09' of the fourth engagement 220. The fifth fastener L10 of the third engagement 200 is clasped with the sixth fastener L10' of the fourth engagement 220 and the second elasticity element 210 is assembled between the third engagement 200 and the fourth engagement 220. The stem cap 240 is connected with an anterior end of the drive stem 230. When the dosage can 250 is disposed on an anterior end of the stem cap 240, the second elasticity element 210 is pressed into a compress state to combine the fourth toothed clutch L09' and the third toothed clutch L09 so that the third engagement 200 and the fourth engagement 220 can not rotate with each other.

On the contrary, when the dosage can 250 is removed from the anterior end of the stem cap 240, the second elasticity element 210 is in an extension state to uninstall the fourth toothed clutch L09' and the third toothed clutch L09 so that the third engagement 200 and the fourth engagement 220 are separated and can be rotated with each other. On the other hand, the fourth engagement 220 is rotated manually to reset the position of drive stem 230 after users removed the dosage can 250.

The first bond element L11 of the third engagement 200 is clasped with the second bond element L11' of the case body 170 so that the third engagement 200 and the case body 170 can not be rotated with each other.

The chute L12' of the drive stem 230 is mounted in the chute opening L12 of the fourth engagement 220. The conformation of the chute opening L12 is corresponding to a cross section of the drive stem 230. The fourth engagement 220 and the drive stem 230 are rotated together with each other through the chute opening L12 and the chute L12'. On the other hand, when the fourth engagement 220 is restricted to rotate, the drive stem 230 is also restricted to rotate.

The third bond element L13 of the can casing 260 is mounted with the fourth bond element L13' of the case body 170 so as to combine the can casing 260 and the case body 170. The can casing 260 is used to prevent from mistakenly touching internal parts of the injector 10 by users so as to affect interaction of internal structure. Besides, the can casing 260 includes a transparent window 261. Users can watch the remainder in the dosage can 250 through the transparent window 261.

A plurality dosage marks L14' of the dose setting 160 is corresponding to the dosage window L14 of the case body 170. More specifically, when the dose setting 160 presets an injected dosage, the injected dosage is shown in the dosage window L14 through the dosage mark L14'. On the other hand, one of the dosage marks L14' is shown in the dosage window L14 depending on the dose setting 160 moved relatively with the case body 170.

The first track L15 of the third linkage 180 is assembled with the second track L15' of the dose setting 160. The dose setting 160 and the third linkage 180 are sliding axially and rotating together with each other through the first track L15 and the second track L15'.

The third ratchet L16 of the third linkage 180 is connected with the fourth ratchet L16' of the case body 170. By the third ratchet L16 connected with the fourth ratchet L16', the third linkage 180 and the case body 170 are rotated with a click sound and to produce a little resistance. It has an advantage with the visual impairment of users for presetting a dosage by themselves through the sound. In addition, the little resistance description above also can prevent a dose setting 160 to rotate by gravity. The following is more detail operation illustration of an injector 10.

Figure 7A:
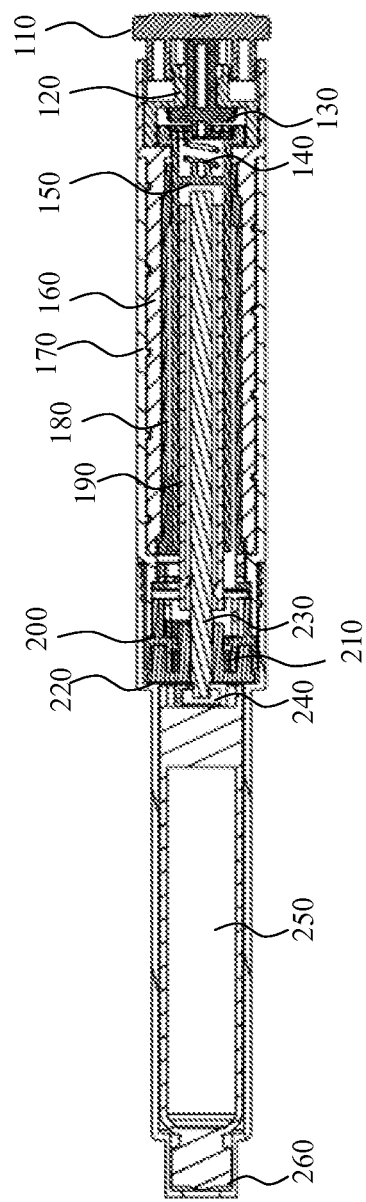
FIGS. 7A to 7D are cross-sectional views of an embodiment of an injector in accordance with the present invention.

FIGS. 7A to 7D are cross-sectional views of an embodiment of an injector in accordance with the present invention. Please refer to FIGS. 7A to 7D in combination. First, the fourth engagement 220 is rotated to reset the position of the drive stem 230, then a dosage can 250 is disposed on the anterior end of stem cap 240 to combine the third engagement 200 and the fourth engagement 220 and to set up a needle (not shown) to the injector then mount on the can casing 260 (as FIG. 7A shown).

Figure 7B:
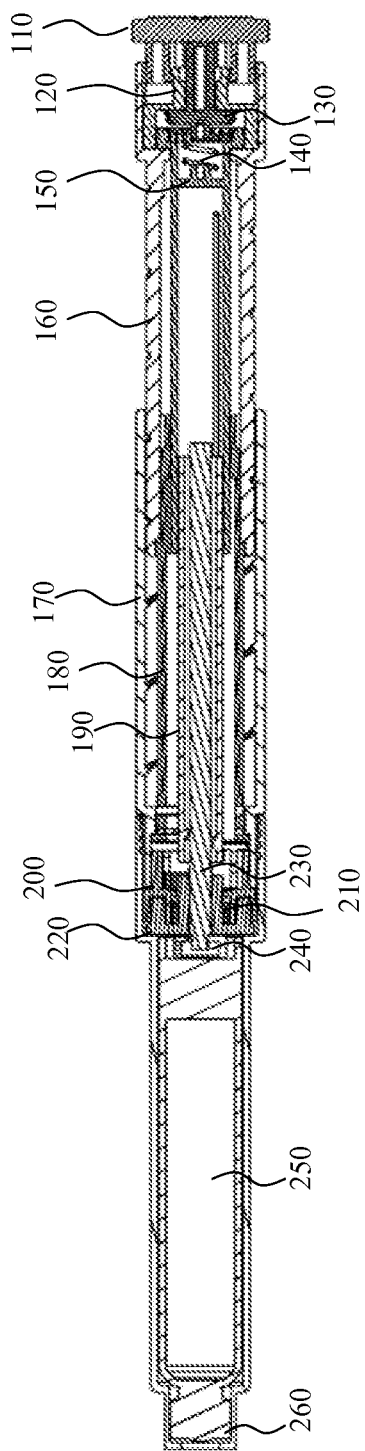

Subsequently, users can hold the case body 170 on one hand and rotate the dose setting 160 exteriorly or interiorly to preset a dose on the other hand (as FIG. 7B shown). Users can see the adjusted dosage from the dosage window L14. To be noticed, the first engagement 130 and the second engagement 150 are separated at this moment so that the process of preset a dose will not move the drive stem 230.

Figure 7C:
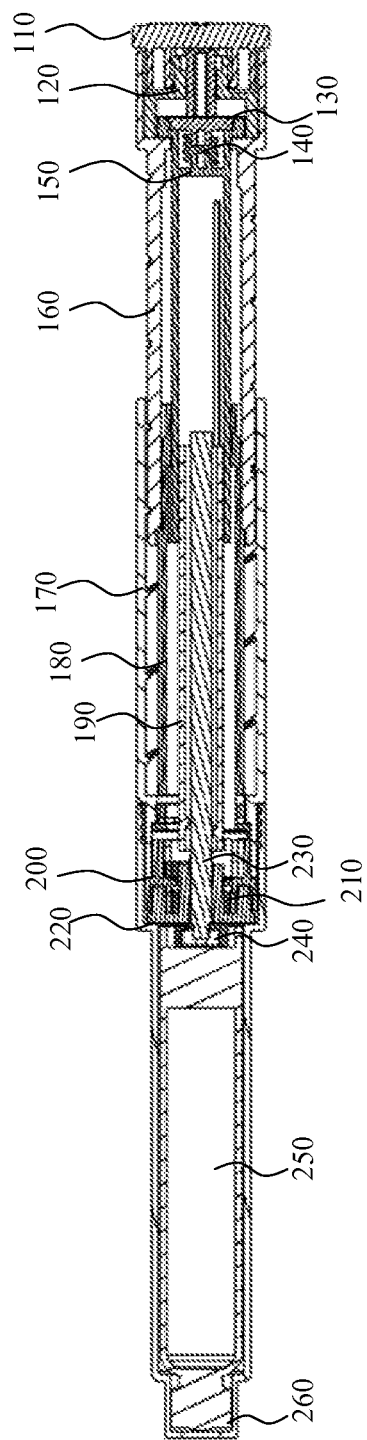

Subsequently, the button 110 is pushed to combine the first engagement 130 and the second engagement 150 (as FIG. 7C shown). To be noticed, after the first engagement 130 and the second engagement 150 are combined so that an action of the dose setting 160 will influence the drive stem 230. On the other hand, before the first engagement 130 and the second engagement 150 are combined, the injector 10 would not be pushed by mistake to cause drugs leaky from the needle so as to make sure accuracy of the injected dosage.

Figure 7D:
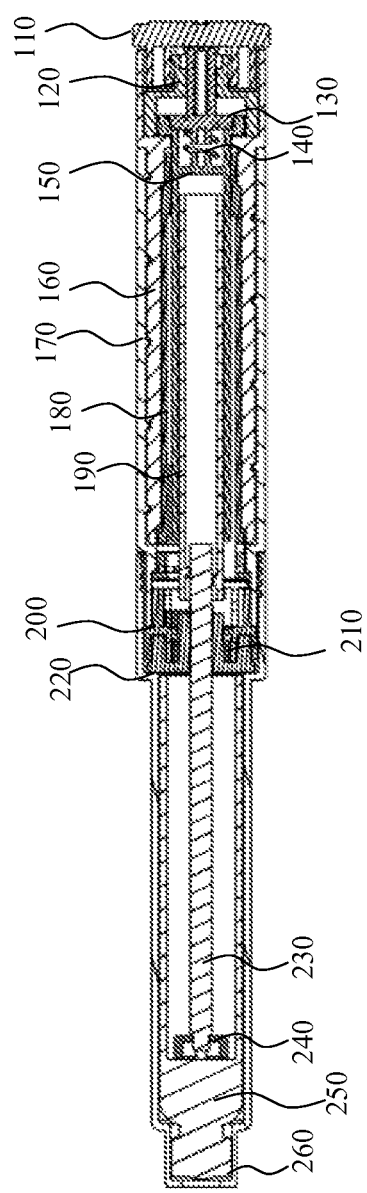

Subsequently, the button 110 is pushed persistently, and the dose setting 160 is rotated interiorly and then to bring the drive stem 230 to move exteriorly so as to push a piston of the dosage can 250 (as FIG. 7D shown). Because of the button 110 and the first linkage 120 will not rotate together so that the process of the dose setting 160 rotated interiorly will not bring the button 110 to rotate.

Although possible types of the injector in accordance with the present invention has been described in the embodiment above, those skilled in the art shall recognized that the injector can be designed differently. Therefore, the spirit of the present invention shall not be limited to these possible types of injector in accordance with the present invention. In other words, the engagement used to connect between the button and the drive stem is the key spirit and scope of the present invention. The followings are some other embodiments in accordance with the present invention for those skilled in the art to know more about the spirit of the present invention.

In the above embodiment, the position, the direction and the distance with the thread of each component in the injector 10 is one choice of the embodiment, but the present invention shall not be limited in it. In the other embodiment, those skilled in the art can change each thread of the direction, the internal or external position or the distance as needed.

In the above embodiment, the third engagement 200, the second elasticity element 210 and the fourth engagement 220 are one choice of the embodiment, the present invention shall not be limited in it. In the other embodiment, those skilled in the art can change the structure as needed. For example, in the other embodiment, the second elasticity element 210 and the fourth engagement 220 can be omitted. When resets the position of the drive stem 230, users can rotate the drive stem directly. In the present embodiment, it designs to free rotate between the drive stem 230 and the stem cap 240 in order to prevent from rotating the dosage can 250 by moving exteriorly of the drive stem 230.

The injector in accordance with the present invention has following advantages.

1. Before a first engagement and a second engagement are combined, the injected dosage can freely preset and the action will not bring a drive stem to move.

2. Users with visual impairment can easy preset a dose through a third ratchet clasped with a fourth ratchet. In addition, it can prevent a dose setting to rotate by gravity.

More exemplary embodiments and advantages of the present invention may be ascertained by reviewing the present disclosure and the accompanying drawing. It is intended that the description and embodiments with reference to the accompanying drawing to be considered as exemplary only.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Other embodiments of the invention will appear to those skilled in the art from consideration of the specification and practice of the invention disclosed herein. It is intended that the specification and examples to be considered as exemplary only, with a true scope and spirit of the invention being indicated by the following claims.

What is claimed is:

1. An injector comprising:
   a case body comprising a first thread;
   a dose setting comprising a second thread and a first fastener, and the second thread assembled to the first thread to let the dose setting move relatively with the case body so as to preset a dose;
   a drive stem comprising a third thread used to push a dosage can;
   a first linkage comprising a second fastener, a first rotatable fastener and a third fastener, and the second fastener clasped with the first fastener;
   a first engagement comprising a fourth fastener and a first toothed clutch, and the fourth fastener clasped with the third fastener;
   a second engagement comprising a second toothed clutch and a first groove, and the second toothed clutch engaged with the first toothed clutch;
   a second linkage comprising a second groove and a fourth thread, and the second groove assembled to the first groove and the fourth thread assembled to the third thread;
   a first elasticity element connected between the first engagement and the second engagement, and the first engagement separated from the second engagement when the first elasticity element is in an extension state; and
   a button comprising a second rotatable fastener clasped with the first rotatable fastener, wherein the button is pushed to compress the first elasticity element so as to combine the first engagement and the second engagement, and then push the dose setting.

2. The injector as claimed in claim 1, further comprising:
   a third engagement comprising a first ratchet, a third toothed clutch, a fifth fastener and a first bond element;
   a second elasticity element; and a fourth engagement comprising a fourth toothed clutch, a sixth fastener and a chute opening, and the fourth toothed clutch clasped with the third toothed clutch and the sixth fastener clasped with the fifth fastener to let the second elasticity element connect between the third engagement and the fourth engagement;

wherein the second linkage further comprises a second ratchet assembled to the first ratchet; the case body further comprises a second bond element clasped with the first bond element; and the drive stem further comprises a chute for axially sliding in the chute opening.

3. The injector as claimed in claim 2, further comprising:
a stem cap connected to an anterior end of the drive stem.

4. The injector as claimed in claim 3, further comprising:
a can casing comprising a third bond element;
wherein the case body further comprises a fourth bond element clasped with the third bond element; when the dosage can is disposed on an anterior end of the stem cap, the second elasticity element is in a compress state to let the fourth toothed clutch combine with the third toothed clutch; when the dosage can is removed from the anterior end of stem cap, the second elasticity element is in an extension state to uninstall the fourth toothed clutch and the third toothed clutch.

5. The injector as claimed in claim 1, wherein the case body further comprises a dosage window, and the dose setting further comprises a plurality dosage marks so that one of the dosage marks is shown in the dosage window for displaying the dose.

6. The injector as claimed in claim 1, further comprising:
a third linkage comprising a first track and a third ratchet;
wherein the dose setting further comprises a second track assembled with the first track; the case body further comprises a fourth ratchet connected with the third ratchet; when the dose setting is rotated, the second track and the first track bring the third linkage to rotate and the fourth ratchet is interfered with the third ratchet.

* * * * *